United States Patent [19]

Speer

[11] 4,040,420
[45] Aug. 9, 1977

[54] PACKAGING AND DISPENSING KIT

[75] Inventor: Spencer J. Speer, Ontario, Calif.

[73] Assignee: General Dynamics, Pomona, Calif.

[21] Appl. No.: 679,426

[22] Filed: Apr. 22, 1976

[51] Int. Cl.² .............................................. A61M 5/00
[52] U.S. Cl. .......................... 128/218 M; 128/218 N
[58] Field of Search ......... 128/218 R, 218 P, 218 PA, 128/218 M, 218 C, 218 N, 218 NV, 221, 220, 215, 216, 232, 239, 272.3, 234; 222/135, 136, 137, 386

[56] References Cited

U.S. PATENT DOCUMENTS

| 2,848,997 | 8/1958 | Miskel et al. | 128/232 |
| 3,640,268 | 2/1972 | Davis | 128/232 |
| 3,828,980 | 8/1974 | Creighton et al. | 128/218 P |

FOREIGN PATENT DOCUMENTS

| 9,324 | 10/1902 | Austria | 128/218 C |
| 419,869 | 10/1924 | Germany | 128/218 M |

Primary Examiner—John D. Yasko
Attorney, Agent, or Firm—Henry M. Bissell; Edward B. Johnson

[57] ABSTRACT

An apparatus for storing and dispensing a plurality of disparate, reactible fluid materials in a relatively viscous state in separate storage locations including means for dispensing the fluid through separate, easily removable needles. A plurality of closely adjacent cylinders have distinct and separate interiors with nozzles formed at one end. Separate removable needles have sealed locking arrangements for attachment to the nozzles. Different designs and structures of the needles are given so that the fluids can be mixed together, joined together or kept separate until injected through needle point openings. Structure is provided for disproportionately mixing the separately contained materials according to the desired mix. Preferably, the dispensing cylinders are formed of transparent material having graduated measuring marks on the liquid-containing portions. The entire apparatus may be constructed of inexpensive materials, such as plastic, the apparatus being intended for disposal after the fluid liquids prepackaged therein have been dispensed.

18 Claims, 8 Drawing Figures

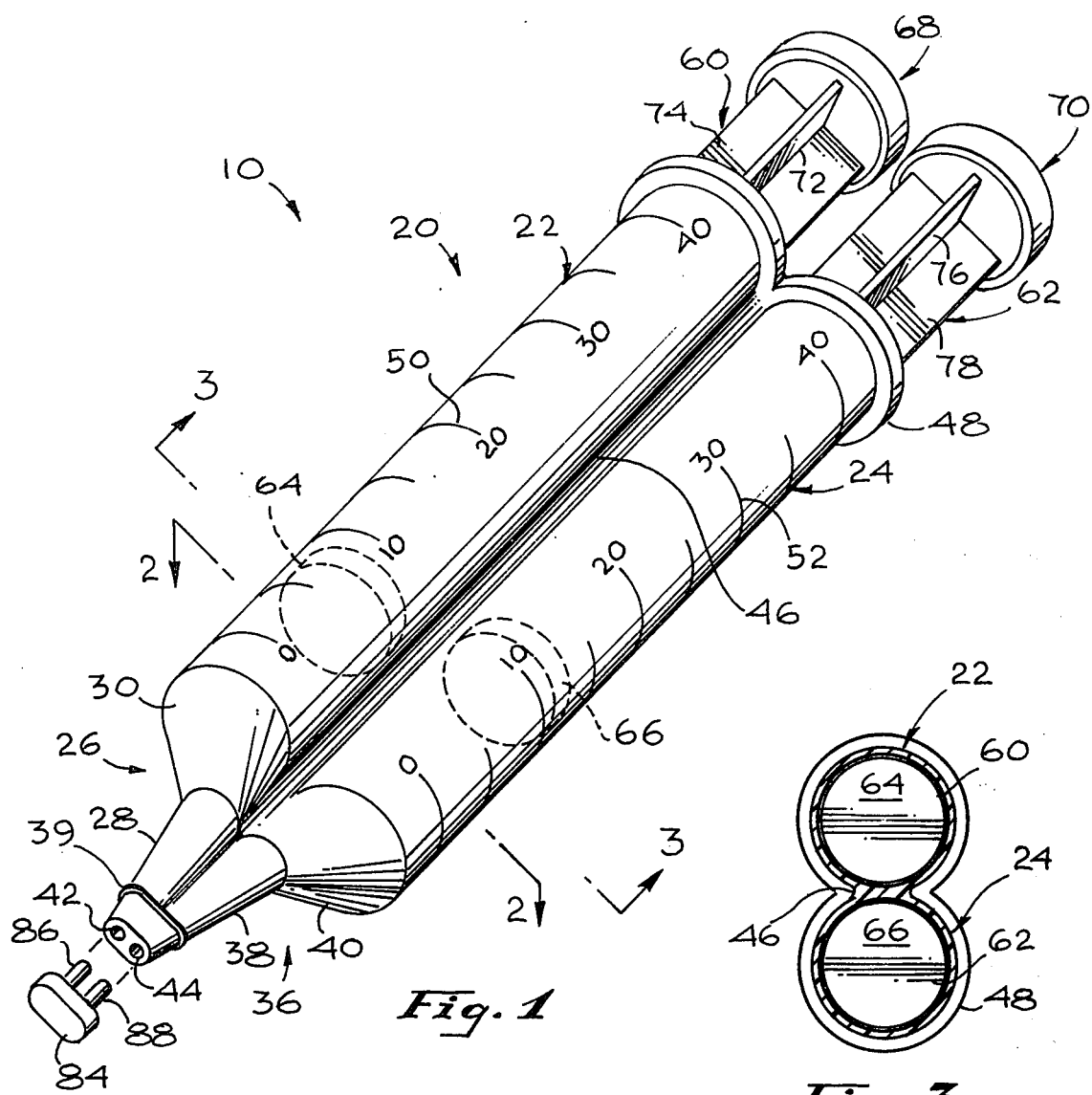
Fig. 1
Fig. 3
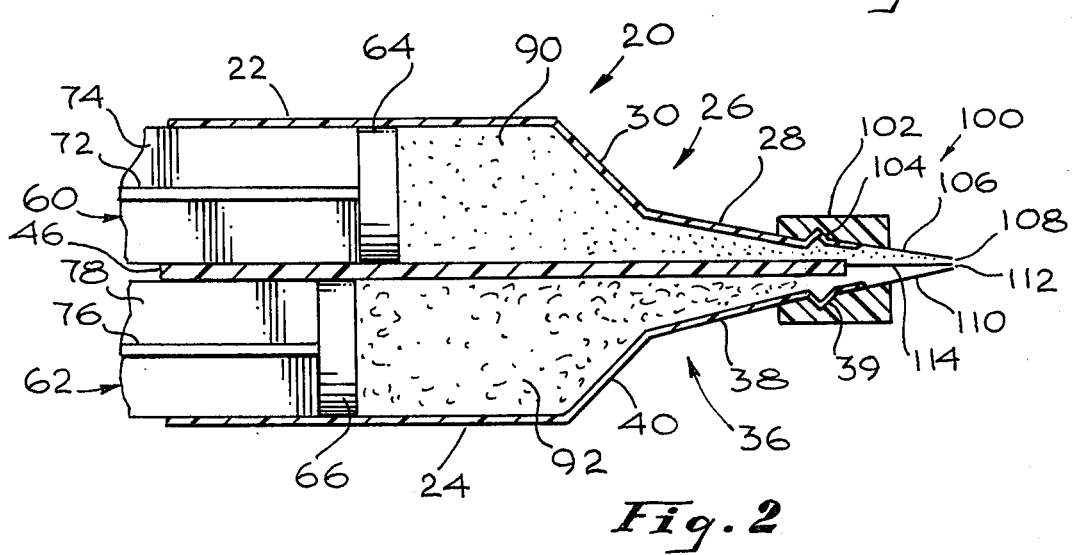
Fig. 2

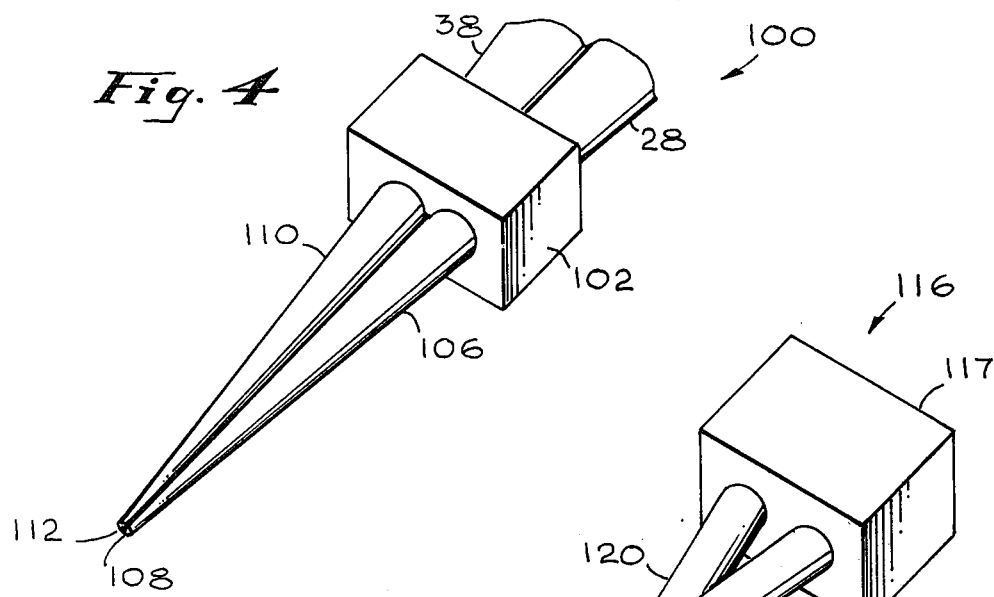
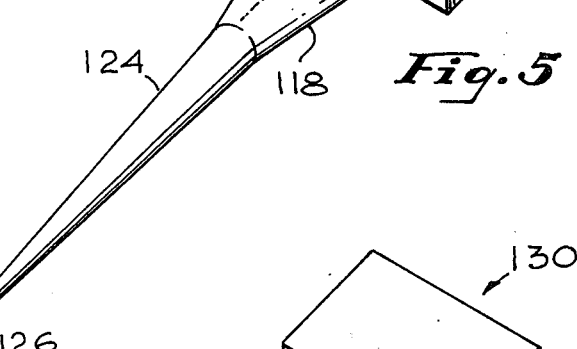
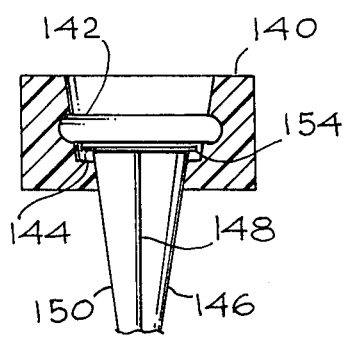
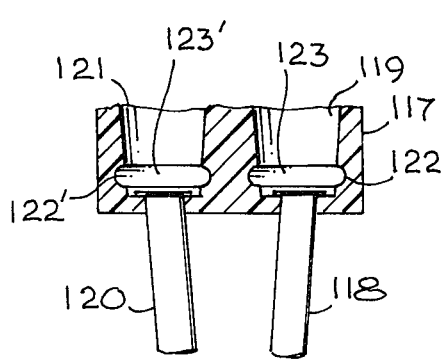

PACKAGING AND DISPENSING KIT

BACKGROUND OF THE INVENTION

1. Field of the Invention

The present invention relates to the field of liquid fluid storing and dispensing apparatuses, and more particularly to manually operated, syringe-type or hypodermic apparatuses for containing and dispensing two or more viscous liquids or fluids at below surface or subcutaneous locations in industrial and health science uses.

2. Description of the Prior Art

There are frequent applications in which it is necessary to store and to dispense quantities of two or more different viscous fluid materials in subsurface or subcutaneous locations. An example of such an application which requires the intermixing of two different liquids at the time of application, and requires separate storage prior to that time, might be the injection of two drugs which when mixed together will react in a synergistic or similar type effect. Another typical example of such an application would be the subsurface injection of an epoxy cement, where the disparate materials necessary for comprising the cement must be kept separately until they are brought to the precise location of cement use. Neither of the two component fluids is by itself hardenable and each may be separately stored for extended periods of time before use.

Frequently in injecting the separate liquids separately to the point of interaction, reaction or mixing, the hypodermic needle is inserted subcutaneously and one substance is injected beneath the surface. When the second material is applied via a second injection, it is not infrequent that the liquid or fluid is injected at a point removed from the point of injection of the first substance. Oftentimes, the separately capped disparate materials are separated from each other so that at the time of application they are not readily available from the same source. In addition, separate injection of the complementing fluids frequently results in the improper ratio or proportion of one fluid to the other in the final mix.

It is sometimes desired to have the fluids mixed in their correct proportion immediately prior to the injection at the point of use. At other times, it is desired to keep the fluids completely separate until they are carried to the actual point of use. In selected cases but not in other cases, it is desired to have the fluids turbulently mixed prior to injection at the point of use. It has long been sought to provide a simple, more convenient means for storing and for dispensing the component liquids of a particular mix while retaining the ability to choose at the last moment whether the components are to be conveyed to the point of use separately, or conveyed to the point of use after being merged, or conveyed to the point of use after being turbulently mixed.

SUMMARY OF THE INVENTION

Apparatus for storing and dispensing a plurality of liquid materials comprises a plurality of elongate, dispensing tubes connected in side-by-side relationship, each tube being adapted for storing and dispensing a different liquid material and having a liquid dispensing nozzle formed at one end thereof, the other end of each tube being open. At least dispensing end portions of the nozzles are radially off-set toward a common point, such dispensing ends being thereby caused to be in close proximity to one another for ease in applying the liquid material and for causing intermixing during application. A separate piston, having a liquid sealing portion, is slidably disposed in each of the tubes, operating portions of the pistons projecting axially from the open ends of the tubes. The pistons are individually operative so that the liquid materials may be dispensed from the tubes in any desired quantity or volume ratio.

More specifically, two liquid storing and dispensing cylinders of substantially the same size are formed integrally to be in one piece. Alternatively, the two tubes may be formed of substantially different diameters when the liquids to be dispensed therefrom are intended to be dispensed in substantially different ratios. The tubes are preferably formed from a transparent material and have graduated liquid measuring scales on at least liquid containing portions thereof. A removable cap having projecting portions for sealing the tube nozzle openings is provided to cap the apparatus between uses.

A needle block assembly is provided for attachment to the dispensing nozzle end of the apparatus. Alternative removable hollow needles in the block assembly are selectively attached to the two nozzles. The hollow needles can be constructed to keep the materials separate, or can be arranged in a structure so that they are intermixed or mixed in a chamber before egress through a single hollow needle to the point of use. Optionally, the liquid storing cylinders may be formed from an inexpensive plastic which may be disposable after the liquids have been dispensed therefrom. The needle block assembly may be constructed of inexpensive materials so as to be disposable after a single use or after a limited number of uses. The disposable needle block assembly may be used with more permanent liquid storing cylinders. Conversely, disposable liquid storing cylinders may be used with a more permanent needle block assembly.

BRIEF DESCRIPTION OF THE DRAWINGS

A better understanding of the present invention may be had from a consideration of the following detailed description, taken in conjunction with the accompanying drawing in which:

FIG. 1 is a perspective view of a syringe-type apparatus for packaging or containing and dispensing two different liquid materials;

FIG. 2 is a sectional view along line 2—2 of FIG. 1, showing the apparatus in cross section, and illustrating the single-piece construction of the storing and dispensing cylinders, plus the addition of the needle pair and block assembly in place;

FIG. 3 is a sectional view along line 3—3 of FIG. 1, showing the cylinder nozzles in longitudinal section;

FIG. 4 is a perspective view of a hypodermic needle block assembly with portions of the syringe-type apparatus in phantom;

FIG. 5 is a perspective view of an alternative embodiment of the needle block assembly of FIG. 4;

FIG. 6 shows yet another alternative embodiment of the needle block assembly of FIG. 4;

FIG. 7 shows an additional alternative embodiment of the needle block assembly of FIG. 4; and FIG. 8 is a cross-sectional view of the needle block assemblies of FIGS. 5 and 6.

DESCRIPTION OF THE PREFERRED EMBODIMENT

As best seen in FIG. 1, a dual syringe-type apparatus 10 for separately containing or storing and dispensing two different viscous liquid materials which are to be used together includes a cylinder structure 20 comprising first and second elongate, rigid tubes or cylinders 22 and 24, respectively. Formed at one end of the cylinder 22 is a dispensing portion 26 which includes a long, slender tapered nozzle 28 and an off-set conical transition section 30 which joins the nozzle to the cylinder 22. The axis of the nozzle 28 is radially off-set from the longitudinal axis of the cylinder 22 such that a side portion 30 of the entire dispensing portion 26 is longitudinally aligned with one side of the cylinder 22 (FIG. 2). In an identical manner, a dispensing portion 36, including an off-set nozzle 38 and a transition section 40, is formed at a corresponding end of the cylinder 24. The nozzles 28 and 38, as seen in FIGS. 1 and 2, are thus off-set toward a common point or plane along the intersection of the cylinders 22 and 24 so that a dispensing opening or aperture 42 in the nozzle 28 is closely adjacent to a corresponding opening or aperture 44 in the nozzle 38. A raised ridge 39 is formed around the exterior surface of the thus-formed nozzles 28 and 38. The purpose of ridge 39 will be explained in greater detail below.

The cylinder structure 20 is formed (for example, by injection molding of a suitable inexpensive plastic material) into a unitary, integrated structure in which the longitudinal axes of the two cylinders are parallel and the two cylinders are in side-by-side contact, the cylinders 22 and 24 being formed with a common wall portion 46 in their region of contact (FIG. 3).

Formed peripherally around the open ends of the two cylinders 22 and 24, remote from the nozzles 28 and 38, is a radial projecting flange 48, which provides for gripping the apparatus during operation. In order that preselected quantities of liquid materials may be dispensed from the cylinders 22 and 24, or so that the liquids may be dispensed in preselected ratios of volume or weight, liquid containing portions of the cylinders are formed or marked with graduated scales 50 and 52 respectively, the scales including convenient graduations of volume (for example, cubic centimeters) or weight (for example, fluid ounces).

To enable dispensing of the liquids, a first piston 60 is slidably disposed in the first cylinder 22, and a similar second piston 62 is slidably disposed in the second piston 24. The first piston 60 comprises a cylindrical head or end portion 64 which closely fits, in liquid sealing relationship, within the cylinder 22. A similar head or end portion 66 of the piston 62 slides, in fluid sealing relationship, within the cylinder 24. Conventional seals, not shown, may be installed around the portions 64 and 66 to prevent leakage past such portions.

At the end of the piston 60 which projects outwardly from the open end of the cylinder 22, is formed a cylindrical bearing portion 68, by means of which the user manually presses the piston into the cylinder 22 for dispensing liquid from the nozzle 28. A similar bearing portion 70 is formed at the corresponding end of the piston 62. For economy of construction and for light weight, the portion of the piston 60 intermediate the head 64 and portion 70, is formed of a pair of slender, intersecting longitudinal web elements 72 and 74. The second piston 62 is formed with similar web elements 76 and 78.

To seal the dispensing openings 42 and 44, there is provided a removable cap or plug 84 having generally cylindrical projectings 86 and 88 configured to fit within the corresponding nozzle openings 42 and 44. To prevent the plug 84, when installed, from becoming cemented to the end of the nozzles 26 and 36, the two openings 42 and 44, as well as the corresponding projections 86 and 88, may be formed having different diameters or in different cross sections so that the plug may be installed only in one way—that is, so that when the plug is installed, the projection 86, for example, can only be installed in the opening 42. Such a construction prevents the possibility of contaminating one of the liquids or substances by accidental introduction of small quantities of the other liquid or substance. Otherwise the projections 86 and 88 may be reversed accidentally, thus introducing small quantities of one liquid into the other liquid. Such a contamination might have serious consequences if the cylinders contain, for example, drugs for health science use.

It is emphasized that the two pistons 60 and 62 are not interconnected or joined together in any manner; they are, therefore, capable of independent, selective operation so that different amounts of liquid material 90 and 92 can separately be dispensed from the cylinders 22 and 24 respectively (by pressing the pistons 60 and 62 into the cylinders). Also, by means of such independent piston operation, liquid may be dispensed from one cylinder without dispensing liquid from the other. In this manner, as may sometimes be desired for external measuring or weighing of the liquids, liquid may be dispensed from one of the cylinders 22 and 24 before it is dispensed from the other.

By enabling completely independent advancing of the pistons 60 and 62, liquids having different mixing ratios are easily accommodated in cylinders 22 and 24 having the same internal diameter, and which therefore utilize the identical pistons. If, for example, the liquids 90 and 92 are to be mixed in the ratio of two parts of liquid 90 contained in cylinder 22 to one part of liquid 92 contained in cylinder 24, the cylinder 24 may be prefilled only half as full as the cylinder 22. For dispensing the piston 60 is then advanced twice as far as the piston 62.

However, the close side-by-side configuration of the two cylinders 22 and 24, and hence of the pistons 60 and 62, enables a user to push both pistons into the cylinders in unison, thereby permitting simultaneous dispensing of the liquids from the cylinders 22 and 24 in the ratio determined by the cylinder diameters.

If it is desired to depress the pistons 60, 62 simultaneously, yet have a disproportionate amount of one of the materials dispensed relative to the other material, one cylinder may be constructed having twice the cross-sectional area of its immediately adjacent cylinder. Similarly, the tapered nozzle may, within its taper, have a cross-sectional area proportionately larger than the adjacent tapered nozzle, although such is not essential. In such a manner, the pistons can be depressed at the same rate while a disproportionate share of material is dispensed at the nozzle end. The disproportionate share will be directly related with the ratio of the cross-sectional areas of the pistons.

FIG. 2 shows the needle block assembly 100 in cross-sectional view. A block 102 is formed having an annular or circular groove 104 around its interior opening. The annular groove 104 is shaped to fit snugly and tightly over the ridge 39 constructed on the nozzles 28 and 38. The needle block assembly 100 has projecting needles 106, 110 each having corresponding openings 108 and 112. Interiorly of the assembly 100, the individual needles 106, 110 are separated by a common dividing wall portion 114.

The needle block assembly 100 may be seen in greater detail in the perspective view of FIG. 4 where like reference numerals will be used to identify like elements for ease of understanding the invention and the drawings. Thus in FIG. 4 block 102 has needles 106, 110 projecting therefrom. The needle 106 has an opening 108, while needle 110 has an opening 112. Each opening allows the liquids to flow from the interior conduits of the needles 106, 110.

In operation, the block 102 is fitted over the nozzle ends 28, 38 so that the groove 104 fits tightly over the annular ridge 39 on the nozzles 28, 38. The snug fit of the groove 104 with the ridge 39 presents a fluid tight seal so that the fluids within the cylinders 22, 24 will not escape through the seal. It is preferred, therefore, that the block 102 be constructed of some resilient material such as a resilient plastic or rubber. Moreover, the interior opening of the block 102 should be very close fitting over the exterior surface of the nozzles 28, 38.

When the block 102 is fitted on the nozzles 28, 38, the opening 42 will pneumatically connect with the interior conduit of needle 106. Similarly, the opening 44 of nozzle 38 will pneumatically connect with the interior conduit of needle 110. The interior separating wall 114 will fit carefully with the common wall portion 46 between the storing cylinders 22, 24. The interior conduits of the corresponding needles 106 and 110 are kept separate throughout. In operation the point of the needles 106, 110 is inserted beneath the surface and to a point of use of, for example, the epoxy cement. The pistons 64, 66 longitudinally move to force the fluids 90, 92 through the openings 42, 44 and into the corresponding interior conduits of the needles 106, 110. The fluids or liquids 90, 92 are not mixed until they have egressed from their corresponding opening 108, 112. The mixing of the fluids outside the needle openings 108, 112 causes the fluids to set.

FIG. 5 illustrates in perspective view an alternative form of the needle block assembly seen in FIG. 4 of the drawings. In FIG. 5, needle block assembly 116 is seen having needles 118, 120 projecting therefrom. Needles 118, 120 each have an interior conduit. The needles 118, 120 have their interior conduits merged into single needle 124 having a single opening 126. The needle block 117 differs from needle block 102 in that block 117 has two interior passages to receive nozzles 119 and 121 of separate cylindrical containers, or of containers which may be connected but do not have off-centered nozzles. The interior construction of block 117 can be better seen in the sectional illustration of FIG. 8 in the accompanying drawings. The separate nozzles 119 and 121 are provided with retaining ridges 122 and 122', respectively. When nozzle 119 is inserted into the interior passage, ridge 122 can sealingly fit within groove 123 formed within the first interior passage of block 117. The interior conduit of needle 118 then sealingly interfaces with the opening of the nozzle 119 within interior passage in the block 117. In such a manner, fluid may flow through the nozzle 119 and enter the interior conduit of needle 118 without loss of fluid through the interconnection. Similarly, the nozzle 121 has a ridge 122' designed to sealingly fit within groove 123' formed within the second interior passage of the block 117. In such a manner, fluid flowing through the nozzle 121 is transferred to the interior conduit of needle 120 without leaking. At the same time, however, the joint can be disassembled to permit replacement of the needles, closure of the nozzles for storage or for any other purpose.

In operation, the block 117 may be fitted over the end of the nozzles 119, 121. When the plungers or pistons in the container are maneuvered to compress the liquid through the nozzle 121, the liquid proceeds through the interior conduit of needle 120. Similarly, when the piston is longitudinally moved to force the liquid through the nozzle 119, the liquid proceeds through the interior conduit of needle 118. The moving liquid in needle 120 will mix with the liquid moving in needle 118 in the common interior conduit 124 and through the opening 126.

In FIG. 6 is seen yet another embodiment for a needle block assembly which may be used in substitution of needle block assemblies 100 and 116. Specifically, needle block assembly 130 is similar to needle block assembly 116. Again, like reference numerals will be used in FIG. 6 of the drawings for identical items in FIG. 5 of the drawings for simplicity of identification and ease of understanding of the invention. Thus, block 117 is seen having needles 118, 120. Needles 118, 120 have interior conduits through which liquids or fluids may flow. An additional, single needle 124 is provided having an interior conduit through which liquid or fluid may flow to an opening 26. In the alternative embodiment of the needle block assembly 130, a mixing chamber 132 is seen having a substantial and relatively large cross-sectional area, when compared with the cross-sectional areas of the interior conduits of needles 118, 120 and 124 combined. In operation, fluid flows through the interior conduit of needle 118 into the mixing chamber 132. Simultaneously, fluid flows through the interior conduit of needle 120 into the same mixing chamber 132. The force of the flow from the relatively small cross-sectional area interior conduits of both needles 118, 120 into the greatly expanded cross-sectional area of chamber 132 produces a turbulence which forces the fluids or liquids to mix together into a well-mixed viscous fluid. The well-mixed fluid is then forced through the interior conduit of the additional needle 124 and through opening 126 to the point of use location.

It may be appreciated that the unique structure herein taught is particularly adaptable to the mixing of epoxy cement at the moment of application at the location of use, where the viscous liquids comprising the component parts of the epoxy cement can be kept in separate storage chambers until their use as a cement is desired. At such times as the application of the epoxy is desired at a sub-surface point or location, the needle block assembly 116 or 130 may be fitted over the nozzles 28, 38 of the syringe-type apparatus 10. The needle 124 can be inserted through a surface into a subsurface location. The pistons 64, 66 can be longitudinally moved within the corresponding cylinders 22, 24 to force the liquids in the desired ratios through the needles 118, 120 in the needle block assemblies. The fluids or liquids will then mix either in the mixing chamber 132 or at the point of confluence in needle block assembly 116. In any event, the mixed fluids will then be forced through the interior conduit of needle 124 and through the opening 126 which has been positioned beneath the surface punctured by the needle 124.

Later it may be found after a moment of nonuse that the epoxy cement has set within the mixing chamber 132, within the single additional conduit 124, or around the openings 108, 112 so as to block the further flow up of liquids through these elements. In such event, the block assembly can be removed from the nozzles 28, 38, and replaced by a fresh block assembly. If the block assemblies are constructed of inexpensive materials which are readily disposable, a fresh block assembly may be installed for each separate use of the syringe-type apparatus 10.

In other uses of the invention it may be desired to have a permanently constructed needle block assembly, while having an easily disposable storage cylinder arrangement. For example, in health science uses a very carefully constructed needle suitable for insertion in the hypodermis may be desired. Such a needle, it may be appreciated, should preferrably be made of some permanent metal which may be easily sterilized and reused. Doses of fluids or liquids can be kept in the separate storage cylinders 22, 24. In one embodiment, the openings 108, 112 can be inserted in the hypodermis of skin. In other embodiments, the single needle 124 can be inserted so that its opening 126 will be in the hypodermis. In either event, the movement of the cylinders 64, 66 will force two separate synergistic drugs for reaction in the subcutaneous or hypodermis regions. The reaction of the synergistic, disparate drugs can be delayed, therefore, until they are mixed either at the point of contact after the drugs separately egressed through openings 108, 112 or when the drugs are mixed in the interior conduit of needle 124 or in the mixing chamber 132. After the doses, which are carefully measured in the storing cylinder 22 and the storing cylinder 24, have been completely expelled into the hypodermis or subcutaneous region, the syringe-type apparatus 10 can be removed from the needle block assembly. The syringe-type apparatus 10 can then be disposed of, and the needle block assembly can be sterilized for further use.

Even though the structure 20 is preferably molded as a single, unitary structure for economy of construction, the cylinders 22, 24 may be separately formed and thereafter be submitted or otherwise joined or mechanically held together in the relationship illustrated in the figures. Similarly, the needles 106, 110 may be molded as a single, unitary structure. In an alternative embodiment, as seen more clearly in FIG. 7 of the drawings, the needle itself may be separated from the locking block. In particular, block 140 is seen in cross-sectional view. Block 140 has an interior annular groove 142 so that when the block 140 is positioned around the nozzles 28, 38 the interior groove 142 fits snugly over the raised ridge 39. The block 140 is distinctly separate from needles 146, 150. The block 140 is constructed having a small annular ridge 144. The needles 146, 150 which may be formed together in a single, unitary structure, are constructed having an annular lip 154. When the needles 146, 150 are inserted through the opening formed by the annular ridge 144, the lip 154 fits against the ridge 144. When the block 140 is inserted around the nozzles 28, 38 so that the interior groove 142 fits snugly and sealingly around the ridge 39, the lip 154 is forced into sealing contact with the annular ridge 144. The snug fit of the needles 146, 150 within the block 140 may be made and forced by the abutment of the interior separation wall 46 against the interior separation wall 148 between the interior conduits of needles 146, 150. In such a manner, the common needle lock block 140 can be repeatedly used, while a fresh needle or needle combination can be inserted for each use as may be desired.

Although there have been described above a specific arrangement of an apparatus for containing and dispensing two or more fluid or liquid materials, with a limited selected number of alternative embodiments in accordance with the invention for the purpose of illustrating the manner in which the invention may be used to advantage, it will be appreciated that the invention is not limited there to. Accordingly, any and all modifications, variations or equivalent arrangements which may occur to those skilled in the art should be considered to be within the scope of the invention as designed in the appended claims.

What is claimed is:

1. Apparatus for storing and dispensing a plurality of disparate inter-reactable fluids from separate storage locations, comprising:
    a plurality of distinct, elongate chambers containing fluids, each chamber including a piston for forceably ejecting the fluid therefrom through a tapered nozzle;
    needle means having a corresponding plurality of interior conduits for dispensing fluid from said nozzles;
    lock means including a ridge projecting about an exterior surface of each tapered nozzle; and
    releasable retaining means comprising a separable needle block having a fluid conduit with an interior groove for engaging a corresponding nozzle ridge and means for retaining associated needle means in sealing relationship with the chamber nozzles and the fluid conduits.

2. The apparatus of claim 1 wherein each tapered nozzle has a center line offset from a center line of its corresponding elongate chamber, each tapered nozzle abutting the tapered nozzle of every other chamber and having an opening adjacent every other tapered nozzle opening, the combination of tapered nozzles defining a common exterior surface thereon; and wherein further the lock means includes an annular ridge formed around the common surface.

3. The apparatus of claim 2 wherein the needle block interior groove is formed to sealingly fit over the annular ridge.

4. The apparatus of claim 1 wherein the needle means has a separate opening for each needle interior conduit, all such openings being positioned close together as a point.

5. The apparatus of claim 1 wherein the needle means has a single opening at a point, the interior conduits merging into a single conduit directing fluid into the single opening.

6. The apparatus of claim 5 wherein the interior conduits merge into the single conduit in an expanded chamber having a substantially increased cross-sectional area relative to the combined cross-sectional areas of the interior conduits.

7. The apparatus of claim 1 wherein the nozzle openings are disproportionate in cross-sectional area to each other in proportion to the ratio of the fluid material from each nozzle opening's corresponding tubular chamber to a predetermined disparate fluid combination.

8. The apparatus of claim 1 wherein each piston may be operated selectively and individually relative to the other pistons, and selectively uniformly in movement with the other pistons.

9. The apparatus of claim 1 wherein the cross-sectional area of each chamber and of its piston is proportional to the cross-sectional area of the other chambers in the ratio of the fluid volume in that chamber to the corresponding fluid volumes in the other chambers.

10. The apparatus of claim 9 wherein the needle means has a separate opening for each needle conduit, with such openings being positioned close together at a point.

11. The apparatus of claim 9 wherein the needle means has an additional opening at a point, the interior conduits merging into a single conduit directing fluid into said single additional opening.

12. The apparatus of claim 11 wherein the interior conduits merge into the single conduit in an expanded chamber having a substantially increased cross-sectional area relative to the combined cross-sectional areas of the interior conduits.

13. The apparatus of claim 1 wherein the needle block has an interior configuration adapted to position the needle means in place aligned with said nozzles when the needle block is mounted with its interior groove engaging said projecting ridge.

14. The apparatus of claim 13 wherein the interior configuration is further adapted to permit the release and replacement of said needle means from the needle block when the needle block is separated from said nozzles.

15. The apparatus of claim 1 wherein the needle means include a tapered exterior surface, and wherein the needle retaining means include a needle opening having a tapered interior surface for mating with the needle means exterior surface and adapted to releasably retain the needle means in sealing relationship in the needle block.

16. The apparatus of claim 15 wherein the needle means further include an outwardly projecting shoulder extending about the portion of the needle means adjacent the nozzles, and wherein the needle retaining means further include an interior recess located between said groove and said opening for receiving said shoulder and retaining the needle means in sealing relationship within the needle block.

17. The apparatus of claim 1 wherein one of the projecting ridge and the material of the needle block defining said interior groove is resilient to permit releasably fitting the groove over the ridge.

18. The apparatus of claim 17 wherein the needle block is of resilient material to permit the groove to fit tightly over the ridge and to establish a sealing relationship between the needle block fluid conduit and the nozzles and the needle means, respectively.

* * * * *